United States Patent
Axelsson et al.

(10) Patent No.: US 10,092,715 B2
(45) Date of Patent: Oct. 9, 2018

(54) DIRECTIONAL USE

(75) Inventors: Anders Axelsson, Bjärred (SE); Karl Olov Fagerström, Kagerod (SE)

(73) Assignee: Niconovum USA, Inc., Winston-Salem, NC (US)

( * ) Notice: Subject to any disclaimer, the term of this patent is extended or adjusted under 35 U.S.C. 154(b) by 1497 days.

(21) Appl. No.: 12/440,817

(22) PCT Filed: Sep. 27, 2007

(86) PCT No.: PCT/EP2007/008420
§ 371 (c)(1),
(2), (4) Date: Jan. 15, 2010

(87) PCT Pub. No.: WO2008/037470
PCT Pub. Date: Apr. 3, 2008

(65) Prior Publication Data
US 2010/0108059 A1    May 6, 2010

Related U.S. Application Data

(60) Provisional application No. 60/951,619, filed on Jul. 24, 2007.

(30) Foreign Application Priority Data

Sep. 27, 2006 (DK) ................................ 2006 01246

(51) Int. Cl.
*A61M 31/00* (2006.01)
*A61M 15/00* (2006.01)

(52) U.S. Cl.
CPC ...... *A61M 15/009* (2013.01); *A61M 15/0021* (2014.02); *Y10T 29/49826* (2015.01)

(58) Field of Classification Search
CPC ..... A61K 9/006; A61K 9/0056; A61J 7/0053; A61M 11/00

(Continued)

(56) References Cited

U.S. PATENT DOCUMENTS 5,080,903 A * 1/1992 Ayache et al. ................ 424/433
5,326,570 A    7/1994 Rudnic et al.
(Continued)

FOREIGN PATENT DOCUMENTS

EP    0697223    2/1996
GB    2 227 659    8/1990
(Continued)

OTHER PUBLICATIONS

International Preliminary Report on Patentability dated Mar. 31, 2009, (Published Mar. 31, 2009) during the prosecution of International Application No. PCT/EP2007/008420.

(Continued)

*Primary Examiner* — Emily Schmidt
(74) *Attorney, Agent, or Firm* — Womble Bond Dickinson (US) LLP

(57) ABSTRACT

Disclosed is a method for oral administration of a liquid containing an active substance to a subject for improved absorption into the subject's bloodstream. It includes the steps of providing a delivery device containing the liquid and having a mouthpiece for directing the liquid in a defined direction during delivery; directing the mouthpiece toward a localized area of the subject's mouth being especially suitable for relatively increased uptake and relatively faster onset of action of the active substance; and delivering a measured amount of the liquid directly to the area using the device. Also disclosed is a spray device that includes a container capable of holding a liquid containing an active substance, and a mouthpiece constructed to dispense the liquid in a defined direction and directly to a localized area of a subject's mouth, the localized area being the oral vestibule.

27 Claims, 8 Drawing Sheets

(58) Field of Classification Search
USPC .................................... 604/514; 128/200.14
See application file for complete search history.

(56) References Cited

U.S. PATENT DOCUMENTS

| | | | |
|---|---|---|---|
| 5,362,496 A | 11/1994 | Baker et al. | |
| 5,955,098 A * | 9/1999 | Dugger, III | 424/435 |
| 2001/0020147 A1 * | 9/2001 | Staniforth et al. | 604/58 |
| 2004/0011822 A1 | 1/2004 | Jennings et al. | |
| 2004/0159326 A1 * | 8/2004 | Fagerstrom et al. | 131/270 |
| 2004/0191322 A1 * | 9/2004 | Hansson | 424/489 |
| 2005/0009882 A1 * | 1/2005 | Farr | 514/343 |
| 2005/0150489 A1 | 7/2005 | Dunfield et al. | |
| 2007/0062517 A1 * | 3/2007 | Barker | 128/200.14 |

FOREIGN PATENT DOCUMENTS

| | | |
|---|---|---|
| WO | WO 99/32081 | 7/1999 |
| WO | WO 99/42083 | 8/1999 |
| WO | WO 00/35295 | 6/2000 |
| WO | WO 02/064109 | 8/2002 |
| WO | WO 03/000324 | 1/2003 |
| WO | WO 03/039518 | 5/2003 |
| WO | WO 03/055486 | 7/2003 |
| WO | WO 2004/064811 | 8/2004 |
| WO | WO-2004/080515 | 9/2004 |
| WO | WO 2005/102287 | 11/2005 |

OTHER PUBLICATIONS

Written Opinion dated Dec. 28, 2007, (Published Mar. 27, 2009) during the prosecution of International Application No. PCT/EP2007/008420.

International Search Report dated Dec. 12, 2007 (published Apr. 3, 2008) during the prosecution of International Application No. PCT/EP2007/008420.

* cited by examiner

DIRECTIONAL USE

This Application is a National Phase Application of International Application No. PCT/EP2007/008420 filed Sep. 27, 2007, which claims priority to Patent Application in DK No. PA 2006 01246, filed Sep. 27, 2006 and claims the benefit under 35 U.S.C. 119(e) of U.S. Provisional Patent Application Ser. No. 60/951,619, filed Jul. 24, 2007.

TECHNICAL FIELD

The present invention relates to a method for administering an active substance via the oral cavity, which method enables a fast onset of action and an improved uptake of the active substance. The active substance is administered in the form of droplets of a liquid composition comprising the active substance or, alternatively, in the form of an aerosol or an atomized liquid comprising the active substance. The improvements are obtained by administering the active substance to a relatively limited part of the oral cavity, namely the oral vestibule, notably the labial and/or the buccal vestibule.

BACKGROUND OF THE INVENTION

The oral and buccal cavity has been used for administration of active substances in many years. This administration route has especially been attractive in order to avoid first pass metabolism or e.g. for dosage forms suitable for application under the tongue in order to obtain a fast uptake (e.g. sublingual administration of glyceryl nitrates for alleviating symptoms associated with angina pectoris).

However, improvements with respect to fast uptake and availability of an active substance are still needed; cf. the following in which nicotine is used as a non-limiting example of an active substance.

BRIEF SUMMARY OF THE INVENTION

The present invention is directed to a system and method for oral administration of a liquid containing an active substance to a subject for improved absorption into the subject's bloodstream.

The method includes the steps of providing a delivery device containing the liquid and having a mouthpiece for directing the liquid in a defined direction during delivery; directing the mouthpiece toward a localized area of the subject's mouth being especially suitable for increased uptake and faster onset of action of the active substance relative to other areas of and/or the whole mouth; and delivering a measured amount of the liquid directly to the localized area using the delivery device.

The method is also used for applying liquid droplets or atomized liquid containing an active substance inside a subject's mouth for improved absorption into the subject's bloodstream, which includes the steps of positioning a spray apparatus containing the liquid and having a mouth piece for spraying the liquid in a defined direction, directing the mouth piece toward the oral vestibule of the subject's mouth, and spraying a measured amount of said liquid into the oral vestibule.

The spray device for administering an active substance to the oral cavity of a subject that includes a container capable of holding a liquid containing an active substance, and a mouthpiece being constructed to dispense the liquid containing the substance in a defined direction and directly to a localized area of a subject's mouth, the localized area being the oral vestibule.

The spray apparatus includes a canister that contains a liquid that includes an active substance, and the canister is equipped with a mouth piece for spraying the liquid into the oral vestibule.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 8 shows the Nicotine plasma level that NicoNovum is focusing on.

DETAILED DESCRIPTION OF THE INVENTION

Figure 1:
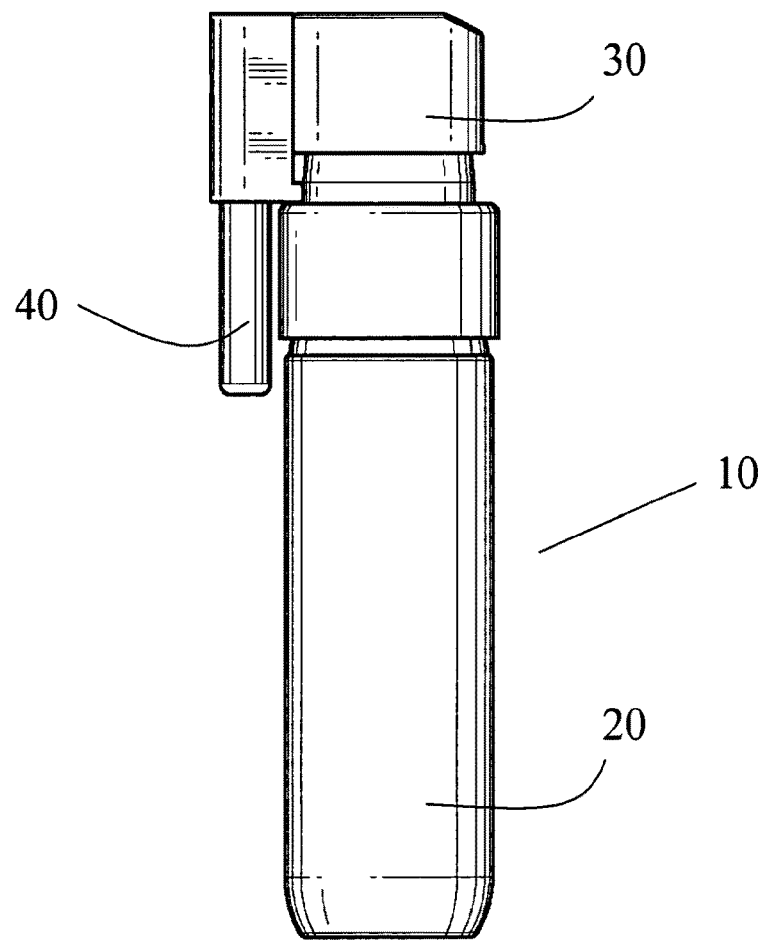
FIG. 1 shows an exemplary embodiment of a delivery device in the form of canister with an atomizing spray mouthpiece adapted to deliver a measured amount of liquid as a spray to a localized area of a mouth. The delivery device 10, comprises a liquid container 20, and an atomizing spray mechanism 30 having a mouthpiece 40.

Nicotine replacement products available today all yield nicotine blood levels significantly lower than smoking or taking wet snuff. A smoker using e.g. 2 mg nicotine gum will only substitute for about 35% of his nicotine blood level when smoking. This level is too low to entirely abolish the abstinence symptoms thus increasing the risk of relapse to smoking.

NicoNovum AB develops products which yield nicotine blood levels more comparable to smoking. The aim is to make it easier to stop smoking by making the decrease in nicotine blood levels less dramatic.

One objective of the development programme is to be able to reach a nicotine plasma level exceeding 6 ng per milliliter within 10 minutes. Such a product would potentially be more helpful in alleviating the withdrawal symptoms, particularly in heavy, more dependent smokers.

That this can indeed be the case is illustrated by the results of a study where the effect on craving symptoms in deprived smokers of nicotine gums with different release profiles were compared; Niaura et al found that a rapid-release nicotine gum reduced cravings more rapidly than a conventional nicotine gum. Reduced cravings are known to be positively correlated with chances to stop smoking.

A rapid-uptake product can therefore be expected to fill a significant medical need in the market.

One product category of interest is mouth spray as this administration form would allow for good dosing flexibility. It is also a type of administration form well liked by consumers.

To this end, the inventors have found that not only is a mouth spray suitable for use in connection with alleviating or treatment of nicotine withdrawal symptoms, but if administered at a specific site in the mouth an increase in onset of action as well as an improved uptake of nicotine are observed. The present invention is based on these findings and provides a method for applying liquid droplets or atomized liquid containing an active substance inside a subject's mouth for improved absorption into the subject's bloodstream, the method comprising the steps of i) positioning a spray apparatus containing the liquid and having a mouth piece for spraying the liquid in a defined direction, ii) directing the mouth piece toward the oral vestibule of the subject's mouth, and iii) spraying a measured amount of said liquid into the oral vestibule.

As seen from the Examples herein, spraying a nicotine-containing liquid into the oral vestibule enhances the onset of action as well as increases the plasma level compared to results obtained after spraying the same liquid (in the same amount and under similar conditions) directly into the mouth. Accordingly, the inventors have found an especially suitable location for administration of active substances via the oral mucosa. It is contemplated that administration to this site, namely the oral vestibule, more precisely the labial and/or the buccal vestibule, even more specific the buccal sulcus, especially the mandubular buccal sulcus, will lead to enhanced onset of action and/or improved plasma levels not only for nicotine, but also for other active substances such as therapeutically, prophylactically and/or diagnostically active substances. Thus, the use of nicotine in the description of present invention serves for illustrative purposes only and is not intended to limit the invention.

In accordance with the above, the present invention provides a method for applying liquid droplets or atomized liquid containing an active substance inside a subject's mouth for improved absorption into the subject's bloodstream, the method comprising the steps of i) positioning a spray apparatus containing the liquid and having a mouth piece for spraying the liquid in a defined direction, ii) directing the mouth piece toward the oral vestibule of the subject's mouth, and iii) spraying a measured amount of said liquid into the oral vestibule, and wherein the time for obtaining a peak concentration ($T_{max}$—oral vestibule) of the active substance in the subject's plasma is obtained faster than that obtained when the spraying is performed directly into the mouth ($T_{max}$—directly), all other conditions being the same.

In the present context, the term $T_{max}$—directly refers to the time it takes for obtaining the maximal plasma concentration after spraying liquid droplets or atomized liquid directly into the mouth. The term $T_{max}$—oral vestibule refers to the time it takes for obtaining the maximal plasma concentration after spraying liquid droplets or atomized liquid into the oral vestibule. The term "faster" means that $T_{max}$ (oral vestibule) is less than about 0.75 $T_{max}$ (directly) such as, e.g., less than about 0.7 $T_{max}$ (directly), less than about 0.6 $T_{max}$ (directly), less than about 0.55 $T_{max}$ (directly) or about 0.5 $T_{max}$ (directly) or less.

In order to achieve a fast onset of action, a fast rise in plasma concentration after administration is normally required and the plasma concentration must be within the so-called effective window, i.e. the plasma concentration must not be so low that no effect is seen and on the other hand not that high that unwanted effects may emerge. Accordingly, a decrease in $T_{max}$ is indicative of a fast onset of action. As seen from the examples herein the rise in plasma levels after application to the oral vestibule are much faster than that obtained after spraying directly into the mouth.

With respect to the envisaged increase in plasma levels after application to the oral vestibule, the examples herein clearly shows that this is the case. Accordingly, the present invention also provides a method for applying liquid droplets or atomized liquid containing an active substance inside a subject's mouth for improved absorption into the subject's bloodstream, the method comprising the steps of i) positioning a spray apparatus containing the liquid and having a mouth piece for spraying the liquid in a defined direction, ii) directing the mouth piece toward the oral vestibule of the subject's mouth, and iii) spraying a measured amount of said liquid into the oral vestibule, and wherein the peak concentration ($C_{max}$—oral vestibule) of the active substance in the subject's plasma is greater than that obtained when the spraying is performed directly into the mouth ($C_{max}$—directly), all other conditions being the same.

In the present context, the term $C_{max}$—directly refers to the maximal plasma concentration after spraying liquid droplets or atomized liquid directly into the mouth. The term $C_{max}$—oral vestibule refers to the maximal plasma concentration after spraying liquid droplets or atomized liquid into the oral vestibule. The term "greater" means that $C_{max}$ (oral vestibule) is more than about 1.05 $C_{max}$ (directly) such as, e.g., about 1.1 $C_{max}$ (directly) or more.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

In keeping with long-standing patent law convention, the words "a" and "an" when used in the present specification in concert with the word comprising, including the claims, denote "one or more." As used herein "another" may mean at least a second or more. Some embodiments of the invention may consist of or consist essentially of one or more elements, method steps, and/or methods of the invention. It is contemplated that any method or composition described herein can be implemented with respect to any other method or composition described herein.

As mentioned above, a method of the present invention is suitable for use when the active substance is a substance that is suitable for use in situations where a fast-onset of action is required. In the literature, numerous examples are given including pain killers, emergency drugs etc. Moreover, numerous drug substances are formulated in sprays or aerosols designed for oral delivery and all those drug substances are contemplated to be suitable for use in a method of the present invention.

In a specific aspect, the active substance is an alkaloid including salts, solvates and complexes thereof, or mixtures thereof. Examples of alkaloids for use in a method according to the invention are nitrogen-containing bases such as, e.g., morphine-alkaloids including morphine, codeine, hydromorphine, tramadol, etc., scopolamine, nicotine-alkaloids including nicotine, lobeline, meclozine, diphenhydramine, cyterisine and analogues and derivatives thereof and promethazin.

In a preferred aspect, the active substance is a nicotine or a salt, solvate or complex thereof, or a mixture thereof.

In the present context the term "nicotine" encompasses nicotine or a nicotine derivative in any form such as, e.g., physical form like amorphous, crystalline, polymorphous etc. or chemical form like isomers and enantiomers etc as well as any salt, complex, derivative or solvate thereof. Nicotine may be selected from nicotine base, nicotine hydrochloride, nicotine dihydrochloride, nicotine monotartrate, nicotine bitartrate, nicotine sulfate, nicotine zinc chloride such as nicotine zinc chloride monohydrate and nicotine salicylate, or it may be selected from nicotine resins such as nicotine polacrilex or e.g. a nicotine-cellulose or cellulose derivative adduct including MCC-nicotine (e.g. nicotine sorbed on microcrystalline cellulose as described in WO 2004/056363).

Although the present invention primarily provides nicotine-containing liquid compositions suitable for use for administration to the oral vestibule and moreover such compositions are in liquid form, it is contemplated that the findings with respect to increased absorption of nicotine from the composition and/or the route of administration between the gum and the cheek in the same manner apply to administration to other active substances. However, a particular interesting composition of the invention is in a form that is suitable for administration to the oral mucosa and in a delivery device that is constructed to deliver the composition to an application site between the gum and the cheek or between the gum and the lips. Such compositions are normally in liquid form including solutions, suspensions, emulsions, dispersions and the like.

It is contemplated that a suitable form of nicotine also may be in the form of a nicotine-carrier adduct or complex such as will be described herein Accordingly, nicotine may be present together with a cellulose material or an ion-exchange material.

The spray apparatus for delivering the liquid containing the active substance may be any suitable apparatus. Thus, spray devices normally employed can be used although modifications with respect to the construction of the mouth piece (or actuator) of the devices are advantageous in order to ensure delivery of the liquid to the correct site, i.e. the oral vestibule. Suitable spray devices or apparatuses include a spray bottle adapted to include the liquid and a top portion including a suitable mouthpiece or actuator. Accordingly, the spray bottle may be of any known type, such as a pump spray or any other means for providing a spray. The spray may be provided by means of a pressurized gas. The spray bottle may have any suitable shape and be made or any suitable material including glass, plastic, and aluminum. The actuator may have different shapes, lengths and directions in relation to the spray bottle and it may be prepared from any suitable material including plastic material or any other material well known within the art to be suitable for this type of device. A suitable actuator comprises an actuator head having a defined axis and being provided with one or more orifice(s) to generate a spray. In an interesting embodiment, the spray pattern generated is a relatively tight pattern, i.e. most of the liquid sprayed is applied to the administration site and, if any, only a minor amount is spread to the surrounding tissue. An example of a suitable device and a suitable actuator is given in FIGS. 1 and 2 and in FIG. 3 is shown how to use the spray device. A suitable device is described in EP-A 1 409 049 which is hereby incorporated by reference. The mouthpiece includes one or more orifice(s) from which the liquid is delivered.

The liquid comprising the active substance may also comprise one or more acceptable excipients.

The one or more acceptable excipients can be carriers, diluents etc. normally employed within the pharmaceutical field. Suitable examples are e.g., solvents, viscosity-adjusting agents, pH-adjusting agents, additives including sweetening agents, taste-masking agents, preservatives, absorption enhancing agents, and mixtures thereof.

Suitable solvents or dispersion media are e.g. solvents that are safe and substantially non-irritating to the oral mucosa. Examples include water, alcohols including ethanol, propanol and isopropanol, glycerin, polyethyleneglycols and the like.

In some embodiments, the viscosity of the liquid may be adjusted e.g. in order to make the liquid more viscous to facilitate spraying of the liquid to the application site. In other situations, it is suitable to decrease the viscosity to make the liquid more thick or to prolong the time period that the liquid stays on the administration site. A possibility is to employ substances known to promote bioadhesion or known to be bioadhesive as such.

Examples of suitable viscosity-adjusting agent are glycerin, cellulose and cellulose derivatives, alginates, pectins, gums, plant extracts, carrageenan and the like.

Normally, it is an advantage if the active substance is present in the liquid in dissolved form. If this is the case, the active substance is present in a form that immediately is available for absorption into the systemic circulation. However, in some cases the dissolution of the active substance does not substantially influence the onset of effect and in such cases the active substance may be dispersed in the liquid. Accordingly, the liquid may be a solution, a dispersion, an emulsion or a suspension or the like. It may also contain nanoparticles, liposomes, microparticles etc.

Buffering Agents

It is well established that a basic pH in the absorption environment in the oral cavity influences the absorption of nicotine. Accordingly, one way of obtaining a basic pH is to include pH adjusting agent in the liquid.

As mentioned above, it is generally known that a slightly alkaline reaction (between 7 and 8) in the oral cavity enhances the absorption of nicotine. Accordingly, it may be and advantage to incorporate a buffer substance in the composition such that a slightly alkaline reaction is provided.

Suitable buffering agents are typically those selected from the group consisting of acetates, glycinates, phosphates, glycerophosphates, citrates such as citrates of alkaline metals, carbonates, hydrogen carbonates, and borates, and mixtures thereof.

If present the one or more buffering agents are present in a concentration from about 0.5% w/w to about 10% w/w, such as, e.g., from about 0.5% w/w to about 7.5% w/w, from about 0.5% w/w to about 5% w/w, from about 0.75% w/w to about 4%, w/w, from about 0.75% w/w to about 3%, w/w or from about 1% w/w to about 2%, w/w.

Sweeteners

In order to increase the sensoric properties of the composition according to the invention one or more sweeteners may be added, such as sugar alcohols including xylitol, sorbitol and/or isomalt, or artificial sweeteners such as e.g. aspartame, acesulfame or saccharin.

The concentration of the one or more sweeteners, if present, is normally at least about 0.05% such as, e.g. from about 0.075% w/w to about 5% w/w or from about 5% to about 35% w/w, such as, e.g., from about 10% w/w to about 35% w/w, from about 15% w/w to about 35% w/w or from about 20% w/w to about 30% w/w.

Anti-Oxidants

It is well-known that nicotine is subject to oxidation and accordingly, it may be advantageous to incorporate one or more anti-oxidants, such as, e.g., ascorbyl palmitate and/or sodium ascorbate, in a composition according to the invention.

The one or more anti-oxidants may be present in a concentration of from about 0.05% w/w to about 0.3% w/w, such as, e.g., from about 0.1% w/w to about 0.25% w/w or from about 0.15% w/w to about 0.2% w/w.

Flavouring Agents

In order to improve the organoleptic properties of a composition according to the invention, the composition may include one or more flavouring agents, such as, e.g., menthol flavour, eucalyptus, mint flavour and/or L-menthol, normally present (total concentration of flavouring agents) in a concentration of from about 0.5% w/w to about 12% w/w, from about 1% w/w to about 10% w/w, from about 1.5% w/w to about 9% w/w or from about 2% w/w to about 8% w/w.

In one embodiment the liquid for use in the present invention comprises
  i) an active substance, notably a nicotine or a salt, complex, derivative or solvate thereof,
  ii) a solvent or a dispersion medium,
  iii) optionally, a viscosity-increasing agent,
  iv) optionally, a taste-masking agent, and
  v) optionally, a sweetener.

In more specific embodiments, the liquid comprises
  i) nicotine or a salt, complex, derivative or solvate thereof,
  ii) a solvent or a dispersion medium,
  iii) optionally, a viscosity-increasing agent,
  iv) optionally, a taste-masking agent, and
  v) optionally, a sweetener.

In specific embodiments, one or more or all of the optional ingredients may be included as well as other suitable ingredients.

The concentration of the active substance, notably the nicotine, or a salt, complex, derivative or solvate thereof, in the liquid is normally at least 0.1% (w/v) and normally less than 90% (w/v). Suitably, the concentration is in a range from about 0.5% (w/v) to about 85% (w/v) such as, e.g., from about 0.5% (w/v) to about 75% (w/v), from about 0.5% (w/v) to about 60% (w/v), from about 0.5% (w/v) to about 50% (w/v), from about 0.5% (w/v) to about 40% (w/v), from about 0.5% (w/v) to about 30% (w/v), from about 0.5% (w/v) to about 25% (w/v), from about 0.5% (w/v) to about 20% (w/v), from about 0.5% (w/v) to about 15% (w/v), from about 0.5% (w/v) to about 10% (w/v), is from about 0.5% (w/v) to about 5% (w/v), such as, e.g., from about 0.5% (w/v) to about 5% (w/v), such as, e.g., from about 0.7% (w/v) to about 4% (w/v), from about 0.9% (w/v) to about 3% (w/v), from about 1.1% (w/v) to about 2% (w/v), from about 1.3% (w/v) to about 1.7% (w/v).

In certain embodiments, the solvent or dispersion medium mentioned in item ii) in the above can be, for example, any alcohol selected from the group consisting of ethanol, propanol, isopropanol, preferably ethanol. The concentration of the solvent, for example alcohol or an aqueous medium or a mixture thereof, is normally at least about 5% (v/v), typically at least about 10% (v/v), at least about 20% (v/v), at least about 30 (v/v), at least about 40 (v/v), at least about 40% (v/v) or at least about 50% (v/v). Thus, it can be from about 60% (v/v) to about 95% (v/v), such as, e.g., from about 70% (v/v) to about 90% (v/v), from about 75% (v/v) to about 85% (v/v).

The viscosity increasing agent mentioned in item iii) in the above can be any viscosity increasing agent suitable for use in fluid compositions. In a preferred embodiment, the viscosity increasing agent is glycerin. The concentration of the viscosity increasing agent, for example glycerin, can be at least about 5% (w/v) such as, e.g. at least 10% (w/v), at least about 15% (w/v) or at least about 20% (w/v) such as e.g. from about 5% (w/v) to about 50% (w/v), from about 10% (w/v) to about 40% (w/v), from about 10% (w/v) to about 30% (w/v).

In order to alleviate any possible unpleasant taste of the composition according to the present invention, a taste-masking agent can optionally be included. Such taste-masking agents can be selected from the group consisting of but not limited to peppermint oil, cinnamon, liquorice, citrus and spearmint, preferably peppermint oil. The concentration of the taste-masking agent, for example, peppermint oil can be from about 1% (w/v) to about 5% (w/v), such as, e.g., from about 2% (w/v) to about 5% (w/v), from about 3% (w/v) to about 4% (w/v), from about 3.5% (w/v) to about 3.6% (w/v).

In the following are given specific liquid compositions included in a spray apparatus according to the invention.

In a specific embodiment the present invention provides a composition comprising
i) an active substance, notably nicotine in a concentration of from about 1% (w/v) to about 20% (w/v),
ii) one or more solvents, notably ethanol in a concentration of from about 5% (v/v) to about 50% (v/v) optionally together with an aqueous medium optionally buffered to pH>7 in a concentration of 20% (w/v) to 75% (w/v)
iii) a viscosity-increasing agent, notably glycerine in a concentration of from about 5% (w/v) to about 35% (w/v),
iv) an artificial sweetener, notably saccharin sodium in a concentration of from about 0.1% (w/v) to about 2% (w/v), notably from about 1% (w/v) to about 2% (w/v),
v) optionally peppermint oil in a concentration of from about 2% (w/v) to about 5% (w/v), with the proviso that the total concentration is 100% w/v.

In another specific embodiment the present invention provides a composition comprising
i) an active substance, notably nicotine in a concentration of from about 1% (w/v) to about 10% (w/v), notably from about 1% (w/v) to about 2% (w/v)
ii) one or more solvents, notably ethanol in a concentration of from about 15% (v/v) to about 25% (v/v) optionally together with an aqueous medium optionally buffered to pH>7 in a concentration of 30% (w/v) to 60% (w/v)
iii) a viscosity-increasing agent, notably glycerine in a concentration of from about 25% (w/v) to about 35% (w/v),
iv) an artificial sweetener, notably saccharin sodium in a concentration of from about 0.1% (w/v) to about 2% (w/v), notably from about 1% (w/v) to about 2% (w/v),
v) optionally, peppermint oil in a concentration of from about 2% (w/v) to about 5% (w/v), with the proviso that the total concentration is 100% w/v.

In another specific embodiment the present invention provides a composition comprising
i) nicotine in a concentration of from about 1% (w/v) to about 2% (w/v),
ii) ethanol in a concentration of from about 75% (v/v) to about 90% (v/v),
iii) glycerine in a concentration of from about 12% (w/v) to about 18% (w/v)
iv) saccharin sodium in a concentration of from about 1% (w/v) to about 2% (w/v),
v) optionally, peppermint oil in a concentration of from about 2% (w/v) to about 5% (w/v), with the proviso that the total concentration is 100% w/v.

In another specific embodiment the present invention provides a composition comprising
i) saccharin sodium in a concentration of from about 1.3% (w/v) to about 1.7% (w/v),
ii) nicotine in a concentration of from about 1.3% (w/v) to about 1.7% (w/v),
iii) ethanol in a concentration of from about 80% (v/v) to about 85% (v/v),
iv) glycerine in a concentration of from about 14% (w/v) to about 16% (w/v)
v) optionally, peppermint oil in a concentration of from about 3% (w/v) to about 4% (w/v), with the proviso that the total concentration is 100% w/v.

The above-mentioned liquid compositions are suitable for use in a spray apparatus for use in a method according to the invention. Normally, a suitable volume to be applied is in a range of from about 50 to about 150 µl such as, e.g., from about 50 to about 100 µl. In the examples herein the volume applied is 70 µl.

The normal dose of nicotine administered is in a range of from about 1 to about 2.5 mg, normally 2 mg provided by 2×70 µl.

Recommended daily dosage is at the most about 30 doses of 2×70 µl.

As mentioned in the above, the present invention provides a composition, the administration of which improves the rate of nicotine-absorption in the bloodstream. The provided improvement relates both to the rate of nicotine-absorption in the bloodstream and to the attained maximum plasma-concentrations of nicotine in the bloodstream.

Nicotine Carriers

In some embodiments a composition of the invention comprises a carrier for nicotine such as mentioned above. The carrier may be a cellulose such as a microcrystalline cellulose ("mcc"). The microcrystalline cellulose may be synthetic or semi-synthetic celluloses, or it may be derived from natural celluloses. Certain specific embodiments may also utilize other forms of carriers, in addition to or including mcc, such as but not limited to fibrous material or carbohydrates including cellulose (including hemicellulose, celluloses with different crystallinities and structures (e.g., varying structures including solid fibers, and addition or including fibers or the like in various structures such as web-like structures and/or other structures), including naturally occurring celluloses including *Cladophora* sp. Algae cellulose or the like), dextran, agarose, agar, pectin, alginate, xanthan, chitosan, starch (including potato starch, shoti starch) etc. or mixtures thereof. While not intended to be bound by theory, it is believed as of the time of this patent application that nicotine may interact with the carrier (for example, mcc or other suitable carrier including other cellulose carriers) by absorbing into and/or adsorbing onto the carrier. Such interaction is completely or nearly completely reversible.

The microcrystalline cellulose may be selected from the group consisting of AVICEL® grades PH-100, PH-102, PH-103, PH-105, PH-112, PH-113, PH-200, PH-300, PH-302, VIVACEL® grades 101, 102, 12, 20 and EMOCEL® grades 50M and 90M, and the like, and mixtures thereof.

Suitable carriers may also be those disclosed in WO 2004/064811, which is hereby included by reference.

More specifically, it is contemplated that a relatively high surface area may be of importance for a carrier that is suitable for use. Accordingly, the specific surface area of suitable carriers is normally at least 0.7 m$^2$/g such as, e.g., 1 m$^2$/g. In certain uses the specific surface area may range between about 0.7 m$^2$/g and at least about 100 m$^2$/g and/or may be anything within this range and/or may be any mixture of sizes within this range. For example, in certain embodiments, the surface area may be about 0.7 m$^2$/g, about 1 m$^2$/g, about 1.5 m$^2$/g, about 2.0 m$^2$/g, about 3.0 m$^2$/g, about 5 m$^2$/g, about 7 m$^2$/g, about 10 m$^2$/g, about 15 m$^2$/g, about 20 m$^2$/g, about 25 m$^2$/g, about 35 m$^2$/g, about 45 m$^2$/g, about 50 m$^2$/g, about 75 m$^2$/g, about 100 m$^2$/g and above about 100 m$^2$/g, or combinations thereof. Such carriers having such suitable surface areas may include, but are not limited to, mcc, fibrous material or carbohydrates including cellulose (including hemicellulose, celluloses with different crystallinities and structures (e.g., varying structures including solid fibers, and addition or including fibers or the like in various structures such as web-like structures and/or other structures), including naturally occurring celluloses including *Cladophora* sp. Algae cellulose or the like), dextran, agarose, agar, pectin, alginate, xanthan, chitosan, starch (including potato starch, shoti starch) etc. and/or mixtures thereof.

In a specific embodiment, nicotine is sorbed on microcrystalline cellulose.

In general, the mean particle size of the carrier such as microcrystalline cellulose is one that is not too low and neither too high such as, e.g., at the most about 500 μm, at the most about 450 μm, at the most about 300 μm, or at the most about 200 μm, or from about 5 to about 500 μm, from 10 to about 500 μm, from 15 to about 500 μm, from about 20 to about 500 μm, from about 30 to about 500 μm, from about 40 to about 500 μm, from about 10 to about 400 μm, from about 20 to about 400 μm, from about 30 to about 400 μm, from about 40 to about 400 μm, from about 30 to about 300 μm, from about 40 to about 300 μm, from about 50 to about 250 μm, from about 50 to about 200 μm or from about 75 to about 200 μm. In specific embodiments the particle size used were about 100 μm. In a preferred aspect, the mean particle size is in a range of from about 15 to about 250 μm such as from about 20 to about 200 μm. In the examples herein a quality of microcrystalline cellulose having a mean particle size of 180 μm has proved to be well-suited for the present purpose.

In an embodiment a composition according to the invention contains nicotine as a nicotine-microcrystalline cellulose carrier complex in which said nicotine is at least partly sorbed on microcrystalline cellulose and/or is at least partially absorbed into the carrier and/or is at least partially adsorbed onto the carrier (e.g., mcc), or mixtures thereof. Such interaction is completely or nearly completely reversible.

Hence, in certain specific embodiments nicotine is sorbed on microcrystalline cellulose, absorbed into the mcc and/or adsorbed onto the mcc, and/or combinations thereof.

In embodiments of the present invention, the carrier (e.g., but not limited to mcc and/or other naturally-occurring cellulose) is at least partially porous. This porosity may be due, for example but not limited to, the structure of the carrier, for example, branched, fibrous, or weblike structures may have pores. Ranges of pore sizes include but are not limited to pore volumes of about 0.01 cm$^3$/g and include, but are not necessarily limited to pore volume ranges of from about 0.003 cm$^3$/g or less to about 0.025 cm$^3$/g, to about or greater than 0.60 cm$^3$/g.

In general, the nicotine carrier complex or nicotine carrier adduct is present in a composition of the invention in a concentration of at least about 2% w/w such as in a range from about 2% w/w to about 98% w/w, from about 2% to about 96% w/w, from about 2% w/w to about 95% w/w, from about 3% w/w to about 90% w/w, from about 4% w/w to about 85% w/w, from about 5% w/w to about 80% w/w, from about 5% w/w to about 75% w/w, from about 5% w/w to about 70% w/w, or from about 7.5% w/w to about 65% w/w.

In certain embodiments, the amount of nicotine sorbed, for example absorbed into and/or adsorbed onto to carrier can be up to 50% or more of the total weight of the composition. Ranges of the amount of nicotine sorbed onto the carrier in the present invention range for less than about 1% of the total weight of the composition to more than about 50% of the composition, including all amounts within this range. While applicants do not intend the invention to be bound by theory, it is believed at the time of preparing this application that the maximum amount of nicotine that can be sorbed onto and/or into the carrier, thereby affecting the amount, for example the percent nicotine by weight of the total composition (e.g., the maximum percentage) is affected by properties of the carrier, including but not limited to the structure of the carrier, the porosity of the carrier, and the surface area of the carrier.

In certain embodiments, the concentration of the nicotine carrier complex or nicotine carrier adduct in a composition of the invention is present in a concentration such as, e.g., from about 80% w/w to about 98% w/w, such as, e.g., from about 85% w/w to about 98% w/w, from about 90% w/w to about 98% w/w, from about 92% w/w to about 98% w/w, from about 93% w/w to about 97% w/w or from about 94% w/w to about 96% w/w.

Other Aspects of the Invention

The present invention also relates to a spray apparatus comprising a canister comprising a liquid comprising an active substance, the canister being equipped with a mouth piece for spraying said liquid into the oral vestibule. The spray apparatus is suitable for use in a method according to the present invention.

The invention also relates to the use of a liquid comprising an active substance for the preparation of a spray apparatus for use in a method according to the invention.

Moreover, the invention relates to a kit comprising
 i) a liquid comprising an active substance,
 ii) a spray apparatus comprising a canister equipped with a mouth piece for spraying a liquid into the oral vestibule, and
 iii) optionally instructions for use thereof, or
a kit comprising
 i) an active substance,
 ii) a liquid,
 iii) a spray apparatus comprising a canister equipped with a mouth piece for spraying a liquid into the oral vestibule, and
 iv) optionally instructions for use thereof.

The kits being suitable for use in a method according to the invention.

All details and particulars described under the main aspect of the invention apply mutatis mutandis to the other aspects of the invention.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Spray Composition with Nicotine

A composition was made from the following ingredients:

| | |
|---|---|
| Nicotine base | 1.00 g |
| Glycerine | 21.02 g |
| Saccharine sodium | 1.00 g |
| Peppermint flavor | 2.50 g |
| Ethanol 99.5% | 14.02 g |
| Buffer pH 8 | 30.5 g (1M solution of K$_2$HPO$_4$) |
| Total | 70.0 g |

All ingredients except nicotine are mixed in a beaker until dissolution. Nicotine is added and stirring is continued for further 15 min.

Figure 2:
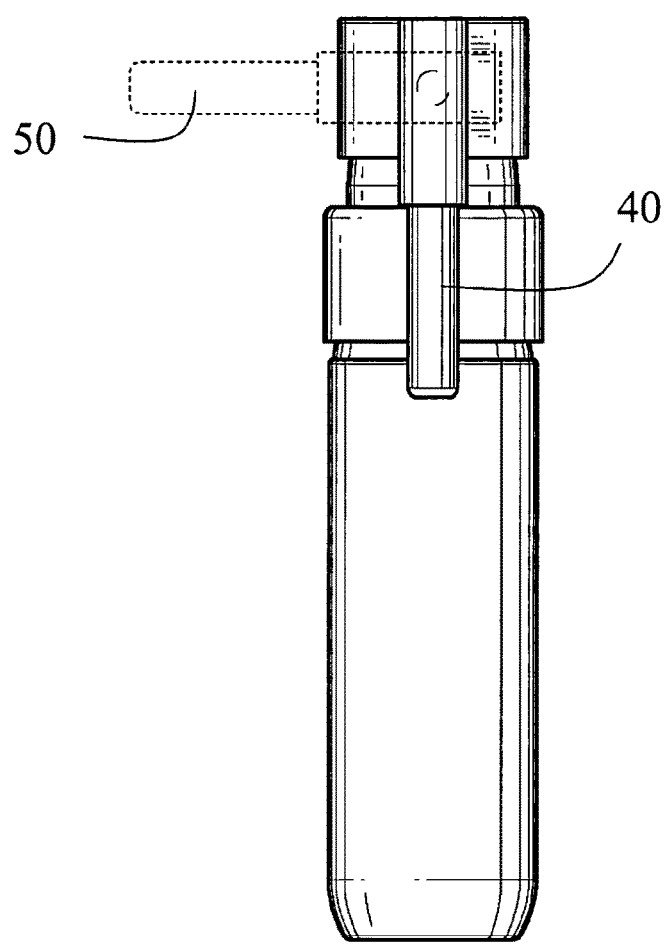
FIG. 2 shows the mouthpiece of the delivery device in FIG. 1 in two alternate positions, folded against the device 40 and extended for use 50.
Figure 3:
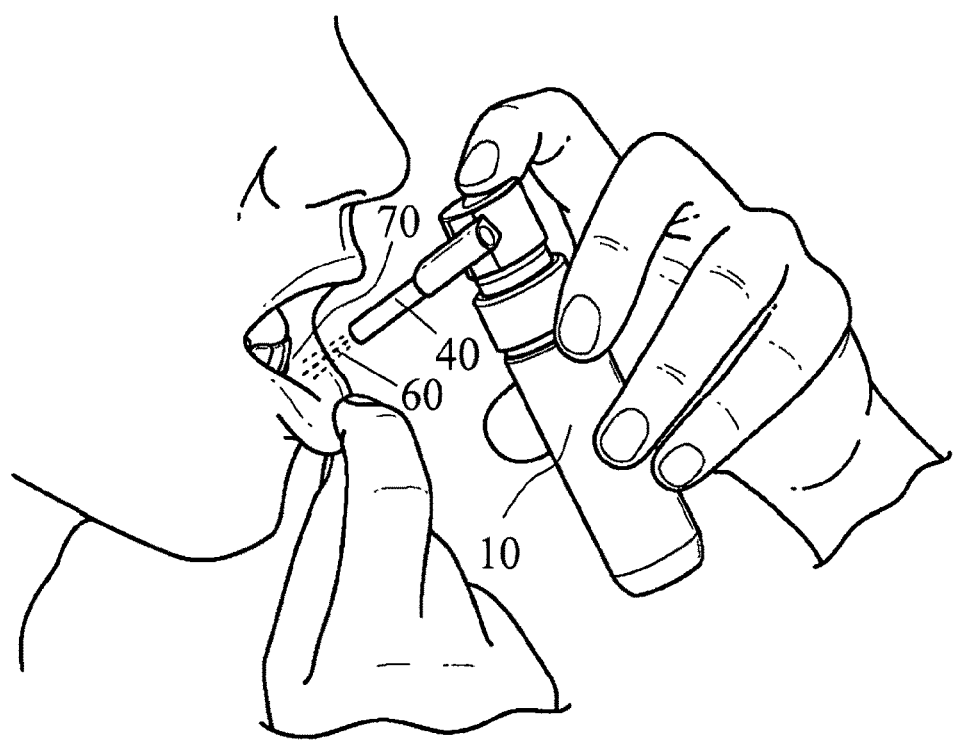
FIG. 3 shows the exemplary delivery device of FIGS. 1 & 2 in use in an example of the methods disclosed herein. Delivery device 10 with mouthpiece 40 extended is positioned to deliver the liquid containing an active substance (e.g. nicotine) to the oral vestibule 70 in the form of an atomized spray 60.

The liquid composition was filled into a device as shown in FIGS. 1 and 2.

Example 2

Application of the Composition of Example 1

Two treatment regimens were tested. In both treatment regimens the composition of Example 1 was used, but in one regimen, the application was via a spray device delivering the composition to the oral vestibule, whereas in the second regiment, the application was via a normal mouth spray delivering the composition to straight into the mouth (see FIG. 3).

Four smokers, one male and three women, mean age 33 years and smoking between 10-20 cigarettes per day participated in both treatment conditions. Both treatments were given on the same day after overnight abstinence with the first early in the morning and the other 5 hours later. No smoking was allowed until both treatments were given. The order of the treatments was balanced.

In the condition between the teeth and lip one spraying was given just left of the frontal teeth in the mouth floor between the gum and lip. A second spraying was applied in the same way just to the right of the frontal teeth. Each spraying gave a dose of 1 mg.

In the straight into the mouth condition the nozzle/mouthpiece of the spray bottle was activated 2 times when it was positioned with its distal part at the teeth line. The spraying was directed approximately at the ovula in the back of the mouth.

Blood samples were drawn from an inserted canula before spraying and thereafter at 5, 10, 15, 20, 30, 45 and 60 minutes.

Figure 4:
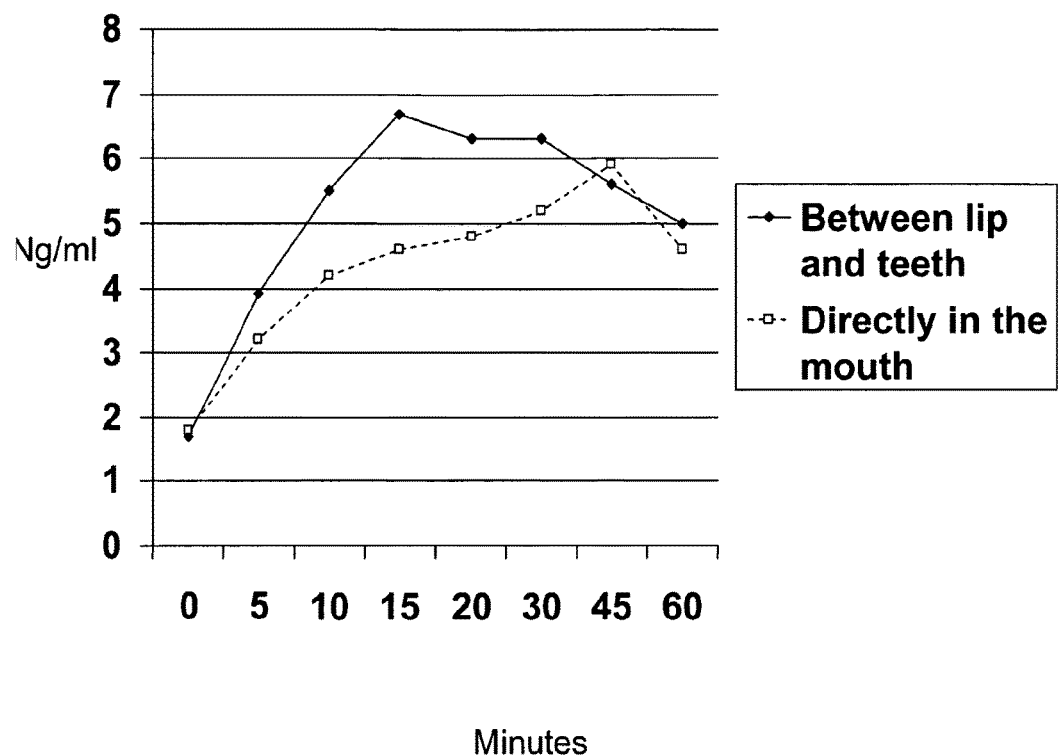
FIG. 4 shows measurements of circulating nicotine concentrations from blood samples drawn from an inserted canula before spraying a liquid containing nicotine as the active substance and thereafter at 5, 10, 15, 20, 30, 45 and 60 minutes. The dashed line with square data points represents circulating nicotine concentrations resulting from a spray directly into the mouth (toward the ovula). The solid line and diamond data points represents circulating nicotine concentrations resulting from a spray directed to the oral vestibule according to the methods disclosed herein.

The results are shown in FIG. 4.

Example 3

Composition A

Composition A was prepared so that 70 µl of the composition contains:

| | |
|---|---|
| Nicotine | 1.00 mg |
| Glycerine | 10.588 mg |
| Saccharin Sodium | 1.00 mg |
| Peppermint oil | 2.50 mg |
| Ethanol 99.5% | 55.931 µl |
| (undenatured ethanol) | (44.30 µg) |
| Water | 1.739 µl |
| (purified water) | (1.74 µg) |

Example 4

Process for Preparation of Composition A

For preparation of 16 liters of composition A, 10190 g Ethanol 99.5%, 400 g water, 2440 g glycerine, 230 g saccharin sodium and 570 g peppermint oil were mixed in a stainless steel container and stirred until complete dissolution.

Then 230 g nicotine was added and the resultant solution was stirred for additional 15 minutes.

The liquid composition was filled into a device similar to that shown in FIG. 1.

Example 5

Composition B

Composition B was prepared so that 70 µl of the composition contains:

| | |
|---|---|
| Nicotine | 1.00 mg |
| Glycerine | 11.088 mg |
| Saccharin Sodium | 0.5 mg |
| Peppermint oil | 2.50 mg |
| Ethanol 99.5% | 55.931 µl |
| (undenatured ethanol) | (44.30 µg) |
| Water | 1.739 µl |
| (purified water) | (1.74 µg) |

Example 6

Process for Preparation of Composition B

For preparation of 16 liters of composition B, 10190 g Ethanol 99.5%, 400 g water, 2440 g glycerine, 115 g saccharin sodium and 570 g peppermint oil were mixed in a stainless steel container and stirred until complete dissolution.

Then 230 g nicotine was added and the resultant solution was stirred for additional 15 minutes.

The liquid composition was filled into a device similar to that shown in FIG. 1.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

Example 7

Nicotine-Containing Mouth Spray

A mouth spray product has the following composition: 14 mg/ml nicotine mouth spray.

| Ingredients | Amount % (m/m) | Amount/ spray dose (mg) | Function | Reference to Standard | Supplier |
|---|---|---|---|---|---|
| Active Substance | | | | | |
| Nicotine | 1.43 | 1.00 | Active ingredient | Ph. Eur. curr. ed. | Siegfried |
| Excipients | | | | | |
| Sucralose | 0.214 | 0.150 | Sweetener | USP/NF curr. ed. | — |
| Mint natural flavour 86% V 808936 | 5.36 | 3.75 | Flavouring agent | — | Robertet |
| Ethanol, anhydrous | 20.0 | 14.0 | Solvent | Ph. Eur. curr. ed. | — |
| Glycerol (anhydrous pure) | 30.0 | 21.0 | Viscosity increaser | Ph. Eur. curr. ed. | — |
| Potassium dihydrogen phosphate | 2.93 | 2.05 (i.e. to achieve a 0.5 M aqueous phosphate buffer solution pH 8.0) | Buffering agent | Ph. Eur. curr. ed. | — |
| Sodium hydroxide | As much as necessary | 0.5 M sodium hydroxide is added to achieve pH 8.0 in the aqueous phosphate buffer solution | Buffering agent | Ph. Eur. curr. ed. | — |
| Purified water | Add to totally 43.0% of the aqueous phosphate buffer solution | Add to totally 30.1 mg of the aqueous phosphate buffer solution | Solvent | Ph. Eur. curr. ed. | — |
| Target Amount | 100 | 70.0 mg | | | |

The composition is filled into a delivery device having a mouthpiece for directing the liquid into the oral vestibule notably the mandibular buccal sulcus.

Example 8

Pivotal Efficacy and Pharmacokinetic Study of the Delivery Device Used According to the Invention The delivery device including the liquid described in Example 7 was subject to a phase III, single blind, randomized, cross-over trial to study the effects of a novel nicotine replacement therapy on the relief of tobacco withdrawal symptoms and user satisfaction. The study centre was Single-centre, Clinical Trials Research Unit, School of Population Health, The University of Auckland.

The objective of the study was:

Part 1a.

A comparison of the withdrawal relief effects of Niconovum mouth spray 2×1 ml per dose with NICORETTE® gum (a nicotine-containing chewing gum product available from GlaxoSmithKline) and placebo lozenge a) To compare the effects of Niconovum mouth spray on withdrawal discomfort and craving after overnight tobacco abstinence with NICORETTE® gum and placebo lozenge. b) To assess subjects' preferences and consumption patterns.

Part 1b.

A comparison of nicotine plasma concentrations and correlation with withdrawal relief of Niconovum mouth spray, NICORETTE® gum and placebo lozenge a) To assess the nicotine absorption rate into plasma of the products b) To assess the relationship between plasma nicotine concentration and withdrawal relief.

Methodology:

Subjects underwent a screening visit prior to the commencement of the study. At this visit they provided written informed consent, completed a short questionnaire collecting demographic data, underwent medical screening (medical history, blood pressure, heart rate, urine dipstick). Eligible subjects were asked to attend 3-5 (Part 1: 3 days; Part 2a: 4 days; Part 2b: 5 days) study days separated by a wash-out period of three days. Subjects were instructed to abstain from smoking from 8 μm the previous evening and try to maintain abstinence over the study day. On each study day subjects were randomly assigned the study medication.

Subjects and investigators were only blind to allocation of spray and placebo. Subjects used the study medication and then rated their level of craving and withdrawal over the first 60 minutes. This was repeated during another 60 minutes immediately following the first and second dose of study medication. Subjects then left the study site and were instructed to use the study medication over the day. They returned to the study site in the evening of the same day to return their medication, report on adverse events and satisfaction and usefulness of the study medication. Subjects were allowed to smoke after these measures were collected. In the 3-day period between study days subjects were asked to smoke as normal.

Number of Subjects (Planned and Analyzed)

Planned: A total of 52 subjects were planned to enter this study Analyzed: A total of 47 subjects attended at least one study day 12 of these people participating in at least one day of part 1b).

Diagnosis and Main Criteria for Inclusion

Subjects who have nicotine addiction. Inclusion criteria were: (1) 18-70 years of age; (2) smoke ≥15 cigarettes per day for the last year; (3) smoke within 30 minutes of waking; (4) Self-report being in good health with verification by a brief screening examination; (5) be able to attend the study site for the duration of the study; (6) be able to read and write English; and (7) subjects are capable of giving informed consent.

Test Product, Dose and Mode of Administration

All drugs under investigation are delivered by the buccal route, two administrations in morning of each study day, and then self-administered for 9 hours on the study day. Part 1 Test product: Niconovum nicotine mouth spray 2×1 mg dose. The dose was administered via a spray device facilitating administration to the mandibular buccal sulcus.

Duration of Treatment:

1 day per week for 3, 4 or 5 study days

Reference Therapy, Dose and Mode of Administration

Reference Products: NICORETTE® 4 mg nicotine gum and placebo lozenge.

Statistical Methods:

The primary outcome (self-reported craving score during each visit between medications) was analyzed using summary statistics (area under the curve). This approach accounts for repeated measurement and results in no loss of information. This approach will include the baseline craving score (average of craving score at 5 and 15 minutes before medication), and period, as covariates. The same approach outlined above for the main analysis of the primary endpoint was also used for the secondary endpoints where cross over measures have been collected. All available data will be utilized. Use of the mixed model was employed to ensure all randomized patients are included in the model. Descriptive statistics were also used to present the raw data collected at baseline and at each study visit.

Figure 5:
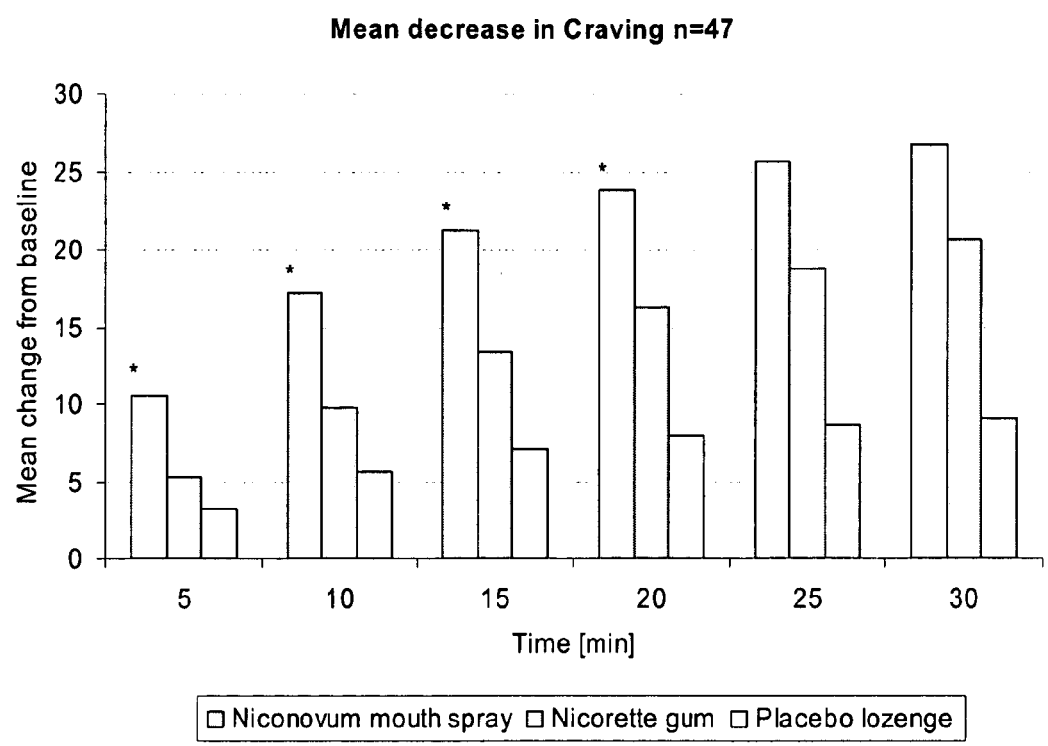
FIGS. 5 and 6 show the results of a clinical trial comparing the effectiveness of a liquid nicotine composition delivered according to the methods herein with NICORETTE® gum or a placebo lozenge. * indicates statistically significant differences between the nicotine liquid composition delivered by the methods herein described relative to the corresponding results using NICORETTE® gum. The graphs are shown as groups of three bars for each criteria representing from left to right: 1) a liquid nicotine composition delivered according the methods, 2) NICORETTE® gum and 3) placebo lozenge.
Figure 6:
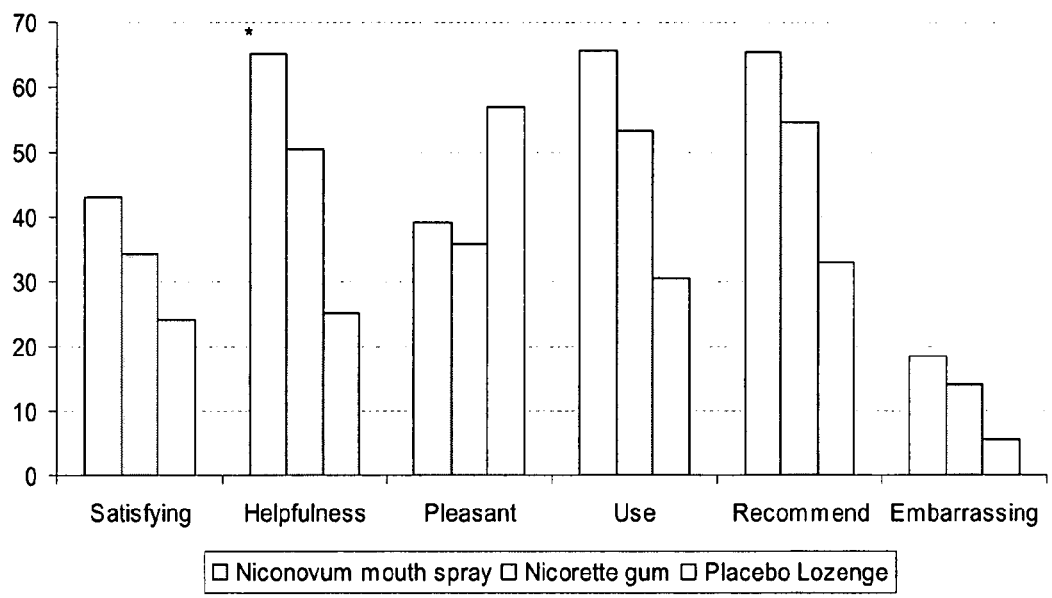
Figure 7:
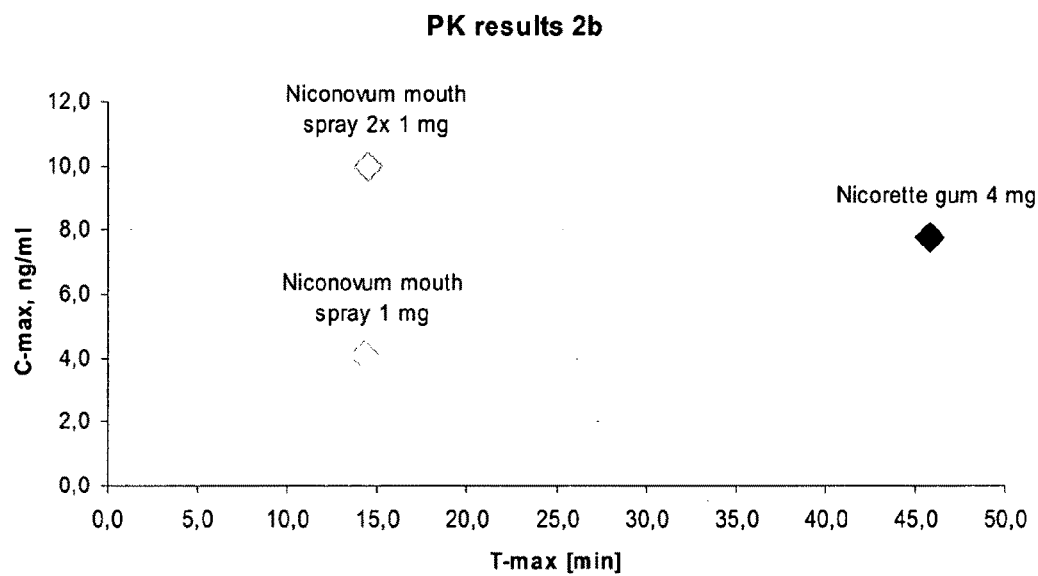
FIG. 7 shows measurements corresponding to the maximum circulating nicotine concentrations from blood samples drawn from an inserted canula as a function of time. Nicotine liquid composition delivered by the methods herein described are compared to NICORETTE® gum.
Figure 8:
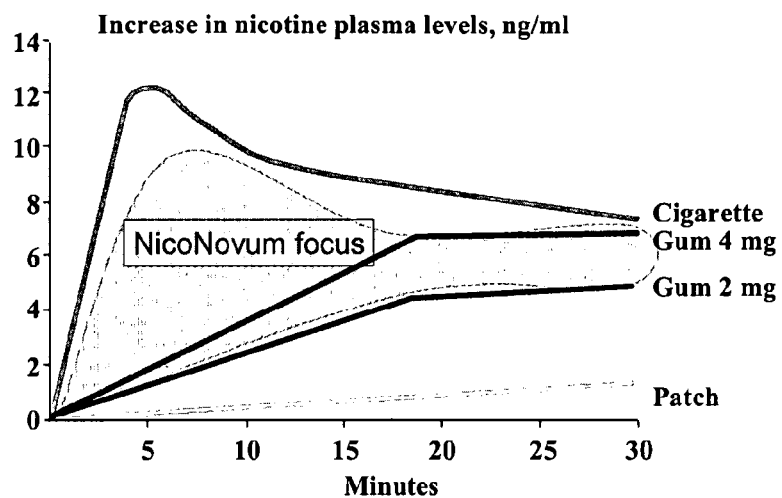

Results:

There was a 26 unit decrease in NICORETTE® gum group and a 29 unit decrease in Niconovum mouth spray group and a 9 unit decrease in placebo lozenge group over the 60 minute period. The differences between the Niconovum product and placebo were found to be significant ($p<0.001$). When the change in craving was analyzed at 5 minute time points during the first 30 minutes, Niconovum mouth spray reduced craving significantly more than NICORETTE® gum and placebo lozenge at 5, 10 and 15 minutes. NICORETTE® gum is more effective than placebo at 20 minutes, and the Niconovum product remains superior to placebo lozenge at the 25 and 30 minute time points. NICORETTE® gum and Niconovum mouth spray are more helpful when compared with placebo lozenge. In addition the Niconovum mouth spray was rated to be more helpful than NICORETTE® gum. The results are shown in FIGS. 5-7.

The foregoing description is intended to be exemplary and not limiting. The invention is defined in the appended claims, which are intended to cover variations, modifications and improvements of the invention.

What is claimed is:

1. A method for oral administration of a liquid containing a nicotine-alkaloid to a subject for improved absorption into the subject's bloodstream, the method comprising:
    providing a delivery device containing the liquid and having a mouthpiece for directing the liquid in a defined direction during delivery;
    directing the mouthpiece toward the mandibular buccal sulcus in the mouth of the subject; and
    delivering a measured amount of the liquid directly to the mandibular buccal sulcus in the mouth of the subject;
    wherein the time for obtaining a peak concentration of the active substance in the subject's plasma after delivery to the mandibular buccal sulcus is obtained faster than that obtained when the spraying is performed directly into the mouth, all other conditions being the same.

2. A method according to claim 1, wherein the nicotine-alkaloid is nicotine or a salt, solvate or complex thereof, or a mixture thereof.

3. A method according to claim 2, wherein the nicotine-alkaloid is selected from the group consisting of nicotine base, nicotine hydrochloride, nicotine dihydrochloride, nicotine tartrate, nicotine bitartrate, nicotine sulfate, nicotine zinc chloride, nicotine salicylate and mixtures thereof.

4. A method according to claim 2, wherein the nicotine-alkaloid is present together with a cellulose material or an ion-exchange material.

5. A method according to claim 1, wherein said liquid comprises the nicotine-alkaloid and one or more acceptable excipients.

6. A method according to claim 5, wherein the one or more acceptable excipients are selected from the group consisting of solvents, viscosity-adjusting agents, pH-adjusting agents, additives including sweetening agents, taste-masking agents, preservatives, absorption enhancing agents, and mixtures thereof.

7. A method according to claim 6, wherein the solvent is selected from the group consisting of water, alcohols including ethanol, propanol and isopropanol, glycerin, and polyethyleneglycols.

8. A method according to claim 6, wherein the viscosity-adjusting agent is selected from the group consisting of glycerin, cellulose and cellulose derivatives, alginates, pectins, gums, plant extracts and carrageenans.

9. A method according to claim 1, wherein said liquid contains the nicotine-alkaloid in dissolved form.

10. A method according to claim 1, wherein said nicotine alkaloid is dispersed in said liquid.

11. A method according to claim 1, wherein the time for obtaining a peak concentration after delivery to the mandibular buccal sulcus is less than about 0.75 of the time for obtaining a peak concentration after spraying directly into the mouth.

12. A method according to claim 1, wherein a peak concentration of the active substance in the subject's plasma after delivery to the mandibular buccal sulcus is greater than that obtained when the spraying is performed directly into the mouth, all other conditions being the same.

13. A method according to claim 12, wherein the peak concentration after delivery to the mandibular buccal sulcus is more than about 1.05 of the peak concentration after spraying directly into the mouth.

14. A method for applying liquid droplets or atomized liquid containing a nicotine-alkaloid inside a subject's mouth for improved absorption in the subject's bloodstream, the method comprising the steps of
(i) positioning a spray apparatus containing the liquid and having a mouth piece for spraying the liquid in a defined direction,
(ii) directing the mouth piece toward the mandibular buccal sulcus of the subject's mouth, and
(iii) spraying a measured amount of said liquid directly into the mandibular buccal sulcus so that the time for obtaining a peak concentration of the nicotine-alkaloid in the subject's plasma after delivery to the mandibular buccal sulcus is obtained faster than that obtained when the spraying is performed directly into the mouth, all other conditions being the same.

15. A method according to claim 14, wherein the nicotine-alkaloid is nicotine or a salt, solvate or complex thereof, or a mixture thereof.

16. A method according to claim 15, wherein the nicotine-alkaloid is selected from the group consisting of nicotine base, nicotine hydrochloride, nicotine dihydrochloride, nicotine tartrate, nicotine bitartrate, nicotine sulfate, nicotine zinc chloride, nicotine salicylate and mixtures thereof.

17. A method according to claim 15, wherein the nicotine-alkaloid is present together with a cellulose material or an ion-exchange material.

18. A method according to claim 14, wherein said liquid comprises the nicotine-alkaloid and one or more acceptable excipients.

19. A method according to claim 18, wherein the one or more acceptable excipients are selected from the group consisting of solvents, viscosity-adjusting agents, pH-adjusting agents, additives including sweetening agents, taste-masking agents, preservatives, absorption enhancing agents, and mixtures thereof.

20. A method according to claim 19, wherein the solvent is selected from the group consisting of water, alcohols including ethanol, propanol and isopropanol, glycerin, and polyethyleneglycols.

21. A method according to claim 19, wherein the viscosity-adjusting agent is selected from the group consisting of glycerin, cellulose and cellulose derivatives, alginates, pectins, gums, plant extracts and carrageenans.

22. A method according to claim 14, wherein said liquid contains the nicotine-alkaloid in dissolved form.

23. A method according to claim 14, wherein said nicotine alkaloid is dispersed in said liquid.

24. A method according to claim 14, wherein the time for obtaining a peak concentration of the active substance in the subject's plasma after delivery to the mandibular buccal sulcus is obtained faster than that obtained when the spraying is performed directly into the mouth, all other conditions being the same.

25. A method according to claim 24, wherein the time for obtaining a peak concentration after delivery to the mandibular buccal sulcus is less than about 0.75 of the time for obtaining a peak concentration after spraying directly into the mouth.

26. A method according to claim 14, wherein a peak concentration of the active substance in the subject's plasma after delivery to the mandibular buccal sulcus is greater than that obtained when the spraying is performed directly into the mouth, all other conditions being the same.

27. A method according to claim 26, wherein the peak concentration after delivery to the mandibular buccal sulcus is more than about 1.05 of the peak concentration after spraying directly into the mouth.

* * * * *